United States Patent [19]

Olivie

[11] 4,025,513

[45] May 24, 1977

[54] SYNTHESIS FOR THE PREPARATION OF TETRACYCLIC COMPOUNDS

[75] Inventor: Jacques Olivie, Gisors, France

[73] Assignee: Akzona Incorporated, Asheville, N.C.

[22] Filed: Feb. 6, 1975

[21] Appl. No.: 547,680

[30] Foreign Application Priority Data

Feb. 9, 1974 Netherlands ............... 7401807

[52] U.S. Cl. .............. 260/251 A; 260/268 PC; 424/250; 424/251

[51] Int. Cl.² ............ C07D 239/70; C07D 241/38

[58] Field of Search .... 260/268 PA, 251 A, 239 D, 260/268 PC

[56] References Cited

UNITED STATES PATENTS 3,190,893  6/1965  Holm .......................... 260/268 TR
3,284,454  11/1966  Haring et al. ............... 260/268 TR

OTHER PUBLICATIONS

P. A. Petyunin Chemical Abstracts, vol. 47, 5385 a–h (1953).
Proctor et al., J. Chem. Soc., 2302–2311, (1957).

Primary Examiner—Donald G. Daus
Assistant Examiner—Jose Tovar
Attorney, Agent, or Firm—Francis W. Young; Hugo E. Weisberger

[57] ABSTRACT

The invention relates to a new synthesis for the preparation of tetracyclic compounds of the general formula:

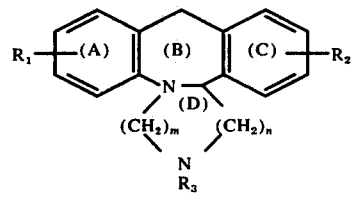

as well as the pharmaceutically acceptable salts thereof, in which:
  $n$ is the number 1 or 2,
  $m$ is the number 1, if $n = 2$ and the number 2, if $n = 1$,
  $R_1$ and $R_2$ stand for hydrogen, hydroxy, halogen, lower alkyl (1–4 C), lower alkoxy (1–4 C) or trifluoromethyl and
  $R_3$ represents hydrogen, alkyl (1–6 C), aralkyl (7–10 C) or an amino alkyl group (1–6 C), in which the nitrogen atom has been substituted by two alkyl groups (1–4 C), or the nitrogen atom forms part of a heterocyclic 5- or 6-membered ring,
having valuable biological properties.

4 Claims, No Drawings

SYNTHESIS FOR THE PREPARATION OF TETRACYCLIC COMPOUNDS

The invention relates to a new synthesis for the preparation of tetracyclic compounds of the general formula:

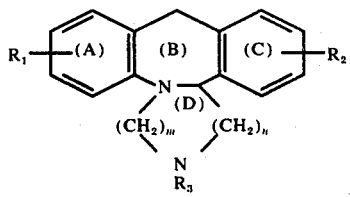

as well as the pharmaceutically acceptable salts thereof, in which:

n is the number 1 or 2 m is the number 1, if $n = 2$ and the number 2, if $n = 1$.

$R_1$ and $R_2$ stand for hydrogen, hydroxy, halogen, lower alkyl (1-4 C), lower alkoxy (1-4 C) or trifluoromethyl and $R_3$ represents hydrogen, alkyl (1-6 C), aralkyl (7-10 C) or an aminoalkyl group (1-6 C), in which the nitrogen atom has been substituted by two alkyl groups (1-4C), or the nitrogen atoms forms part of a heterocyclic 5- or 6-membered ring.

The tetracyclic compounds according to the general formula I are known compounds, described i.a. in the Dutch Pat. No. 129,434 and the Dutch patent application No. 72,12,915. They have very valuable biological properties, especially antiserotonin, antihistamine and antidepressant activities.

Up to now the compounds I have been prepared starting from the tricyclic dibenzo-azepine derivatives of the general formula II:

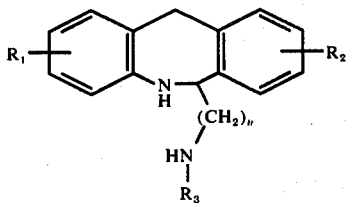

in which $n$, $R_1$, $R_2$ and $R_3$ have the aforesaid meaning.

The starting product II was converted into the final product according to formula I in one step by means of a condensation with, for instance, dihaloethane ($m = 2$), formaldehyde ($m = 1$), and methylene halide ($m = 1$), or in two steps by means of a condensation with, for instance, diethyloxalate ($m = 2$), monochloro-acetylchloride ($m = 2$), ethylchloroformate ($m = 1$), or phosgene ($m = 1$), followed by a reduction of the keto group(s) of the compound thus obtained.

However, these known syntheses do not proceed in a way that is satisfactory in every respect. In practice the "two-steps" condensation reaction appears to be less suitable for production on a large scale, while the "one-step" condensation reaction, particularly in the case of compounds I with $n = 1$ and $m = 2$, does not always result in equally constant yields.

Main objection to these conventional syntheses is, however, the fact that the preparation of the required starting material II is a very time-consuming, multiple-step synthesis which in general gives very poor yields.

The preparation of the starting material II, for instance, in which $R_1$ and $R_2$ are hydrogen and $R_3$ represents methyl is, starting from phtalic anhydride (available on the market), a nine-steps synthesis among which difficult and poorly paying steps such as a substitution to an aromatic nucleus and a Hoffmann-rearrangement have to be carried out. Based on phtalicanhydride the tricyclic starting material II is obtained in 10–12% yield at most, whereas the yield of the tetracyclic final product I, dependent on the method chosen for closing ring D, is 3 to 10%.

When conducting an investigation into more convenient and well-yielding methods in preparing the tetracyclic compounds I, surprisingly a method was found which is based on a fully different concept as compared with the conventional methods described before. The novel synthesis essentially comes to a closure of ring B instead of ring D in the final step of the synthesis.

The novel synthesis is very suitable for production on a large scale. The number of reaction steps required has been halved in regard to the conventional methods, whereas all reaction steps are well-paying and simple chemical conversions.

The final step of the novel synthesis according to the invention is characterized by a ring closure of an intermediate product of the general formula:

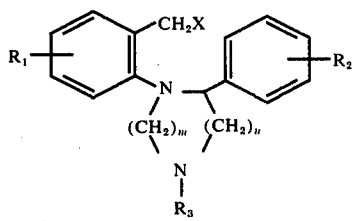

or a salt thereof, in which $n$, $m$, $R_1$, $R_2$ and $R_3$ have the meaning indicated above and X represents a hydroxyl group, halogen (Cl, Br or I) or an etherified or esterified hydroxyl group.

This reaction is performed in a dehydrating or, where X = halogen, dehydrohalogenating medium, preferably at a raised temperature. Dehydrating or dehydrohalogenating agents which are to be added to the reaction mixture for this purpose are i.a. acids such as $H_2SO_4$, concentrated hydrochloride, picric acid, trifluoroacetic acid, phosphoric acid, polyphosphoric acid (PPA), phsophorus oxychloride, phosphorus trioxide or phosphorus pentoxide and Lewis acids (electrophilic agents) such as aluminum chloride, zinc chloride, tin chloride, titanium chloride or boron-trifluoride.

Preferred dehydrating agents are: sulphuric acid, phosphoric acid or derivatives of phosphoric acid, such as phosphorpentoxide and particularly PPA. Aluminum chloride is the preferred dehydrohalogenating agent.

The condensation described above, particularly the ring closure of compounds III, in which X represents a hydroxyl group, affords a very high yield and proceeds almost quantitatively in the case of using a starting compound III, in which $n = 1$ and $m = 2$.

The intermediate compounds III, in which $n = 1$ and $m = 2$, are novel compounds which can be prepared in a surprisingly simple manner by reaction of a compound of the general formula IV:

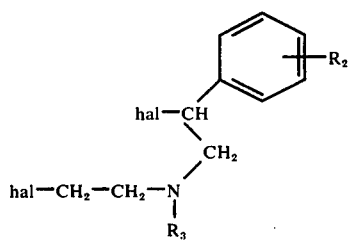

or a salt thereof
in which $R_2$ and $R_3$ have the aforesaid meanings and hal represents halogen, preferably chlorine or bromine, with an aniline derivative of the general formula:

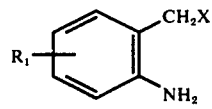

or a salt thereof
in which $R_1$ and X have the aforesaid meanings.

This condensation of compound IV with compound V is carried out in a suitable solvent, preferably at a raised temperature.

A compound V, in which X stands for halogen, should preferably not be used in this condensation because under the reaction conditions required a molecule V (X = halogen) will react with another molecule V (X = halogen) rather than with the compound IV, obviously resulting into lower yields. A compound of the general formula III in which X represents halogen, is therefore preferably prepared by halogenating the corresponding compound III in which X represents a hydroxyl group.

The excellent yields obtained in reacting a compound IV with a compound V in which X stands for a hydroxyl group, is surprising and unexpected. The reactivity of derivatives of benzyl alcohol towards the usual alkylating agents is generally known, so that an alkalation of the hydroxyl group (X) of compound V was more likely.

The compound IV required may be prepared in various manners, for instance starting from products available on the market such as styrene, styrene oxide or mandelic acid.

Thus a compound IV may, for example, be prepared by reacting styrene oxide or a styrene oxide derivative, which has been substituted ($R_2$) at the phenyl nucleus, with the compound $HNR_3$—$CH_2$—$CH_2$—Z, in which $R_3$ has the aforesaid meanings and Z represents a hydroxyl group or halogen followed by halogenating the hydroxy group(s) of the product thus obtained. Another manner consists of the reaction of a β-halo-phenylethylamine derivative or a β-hydroxy-phenylethylamine derivative with dihaloethane or 1-hydroxy-2-halo-ethane, followed by halogenating the hydroxyl group(s), possibly present, of the compound thus obtained.

The preferred synthesis for the preparation of a compound IV is the method in which a β-hydroxy-phenylethylamine derivative of the formula VI:

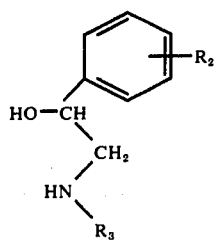

in which $R_2$ and $R_3$ have the aforesaid meanings,
is reacted with ethylene-oxide, after which the hydroxyl groups of the product obtained are halogenated in the usual manner, e.g. with $SOCl_2$, $PBr_3$, etc.

The compound VI is, for example, obtained directly by reacting styrene-oxide with a primary amine ($H_2NR_3$) or indirectly from mandelic acid by converting the acid into the desired amide and reducing the amide obtained into the corresponding amine.

The intermediate compounds III, in which $n = 2$ and $m = 1$ are also novel compounds. These compounds III as well as the compounds III with $n = 1$ and $m = 2$ may be prepared directly by reacting a compound of the general formula VII:

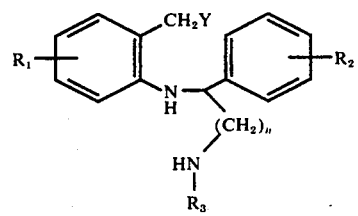

or a salt thereof,
in which $n$, $R_1$, $R_2$ and $R_3$ have the aforesaid meaning
and Y has the same meaning as X defined before except for halogen,
with reagents such as (an aqueous solution of) formaldehyde ($m = 1$), methylene halide ($m = 1$) or ethylene halide ($m = 2$). Obviously this condensation reaction may also be performed with reagents containing an oxo group, such as phosgene ($m = 1$), alkylhaloformate ($m = 1$), dialkyl carbonate ($m = 1$), monohalo acetyl halide ($m = 2$), dialkyloxalate ($m = 2$), etc. The oxo group(s) in the condensation product thus obtained must, however, additionally be reduced to obtain the desired compound III. For these condensation reactions is referred to the Dutch Pat. No. 129,434 and the Dutch patent application No. 72,12,915 in which such condensation reactions have been described for the formation of the D-ring, starting from tricyclic starting substances.

If the compound VII is used for preparing compounds III, a compound III in which X = halogen, is obtained by halogenating the corresponding compound III, in which X = hydroxy.

The, as far as known, novel compounds of the general formula VII may be prepared in a simple manner by reacting a compound of the formula VIII:

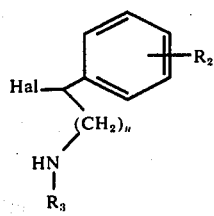

or a salt thereof,
in which $n$, $R_2$ and $R_3$ have the aforesaid meanings and hal represents halogen, preferably chlorine or bromine,
with an aniline derivative of the general formula IX:

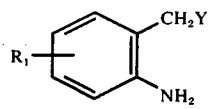

or a salt thereof,
in which $R_1$ and Y have the aforesaid meanings.

The compounds VIII required may be prepared in various manners starting from products available on the market such as styrene, styrene-oxide, mandelic acid, cinnamic acid or benzoyl acetic acid. Thus the compound VIII, for example, may be prepared from β-hydroxy-phenylethylamine (directly available from styrene oxide) or from γ-hydroxyphenylpropylamine (to be prepared in 2 steps from ethylbenzoylacetate or in 3 steps from cinnamic acid) by halogenation of the hydroxyl group.

The methods according to the present invention are further explained in the attached flow sheet.

It is self-evident that the present novel method for the preparation of the compounds I is not restricted to that sequence of reaction steps and to those reagents which are indicated in the flow sheet. In special cases, dependent on the final compound I that is to be prepared and on the starting products that are available, it is very well possible to perform the reaction steps in another sequence or to use other reagents which, whether or not followed by an additional chemical reaction, have the same result as indicated in the reaction scheme.

The reaction routes mentioned above for the preparation of the compounds I mean a considerable reduction of time in comparison with the conventional methods. This particularly applies to the reaction route indicated on the left side of the attached flow sheet for preparing compounds I with $n = 1$ and $m = 2$. Instead of the 10 to 11 reaction steps starting from phtalic acid anhydride, the compound I ($R_1$, $R_2$ = H, $R_3$ = $CH_3$, $n = 1$, $m = 2$) may now be prepared in 4 or 5 steps starting from example from styrene oxide, which is obtainable on the market in large quantities. Thanks to the relatively simple chemical reactions which are applied in the novel synthesis, the yield in comparison with the conventional method of preparation, has been improved by at least 300 to 400%.

The compounds I have an asymmetric carbon so that they can be obtained as racemic mixtures or as optically active compounds. The optically active compounds I may be prepared by resolution of the racemic compounds I. However, these enantiomers I may also be prepared in a direct way by carrying out the resolution in an earlier stage of the the synthesis, for instance, on the compounds with formulae III or VII.

With salts in the present invention are meant the pharmaceutically acceptable acid addition salts obtained by reaction of the free base I with an anorganic or organic acid, such as hydrochloric acid, sulphuric acid, acetic acid, maleic acid, fumaric acid, citric acid, ascorbic acid, etc. Pharmaceutically acceptable quaternary ammonium salts, particularly the (1–4 C) alkyl ammonium salts, are obtained by reaction of the free base I with an alkylhaldide, preferably methyliodide. The latter salts have a marked antihistamine and antiserotonine activity.

In the examples the following nomenclature and numbering with regard to the final products according to formula I has been used:

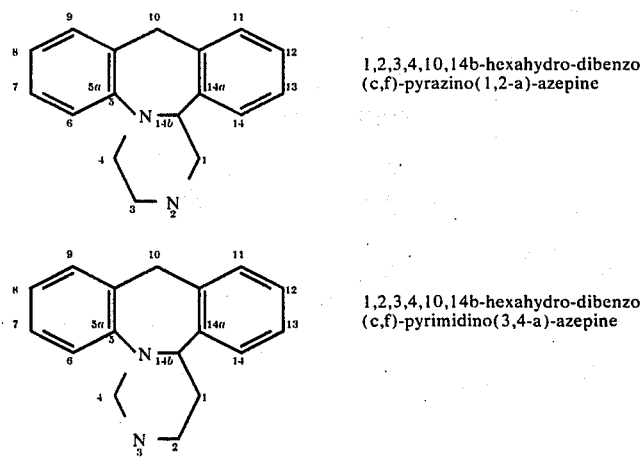

1,2,3,4,10,14b-hexahydro-dibenzo (c,f)-pyrazino(1,2-a)-azepine 1,2,3,4,10,14b-hexahydro-dibenzo (c,f)-pyrimidino(3,4-a)-azepine

EXAMPLE I

Preparation of 2(N)-methyl-1,2,3,4,10,14b-hexahydro-dibenzo (c,f)-pyrazino(1,2-a)-azepine, HCl salt and iodomethylate 1. 1(N)[(0-hydroxymethyl)-phenyl]-2-phenyl-4(N')-methylpiperazine.

To 2.3 g of β-chloro-N-methyl-N-chloroethyl-phenylethylamine in 2 ml of dry dimethylformamide a solution of 1.23 g of 0-amino-benzylalcohol in 3 ml of dimethylformamide is added dropwise at room temperature. This mixture is stirred for half an hour at room temperature. Then 0.8 ml of pyridine is added and the mixture heated to about 70°–80° C. After stirring for half an hour at this temperature, the mixture is cooled down, added to water and the aqueous mixture washed with ether. The aqueous solution is then made alkaline with the aid of sodium carbonate and after the extracted with ether. The ether extracts obtained are washed with water (to neutral) dried and evaporated.

Yield: 2.1 g (75%); melting point 90°–95° C.

Rf in benzene: ethylalcohol (9:1) = 0.29.

2. 2(N)-methyl-1,2,3,4,10,14-b-hexahydro-dibenzo(c,f)-pyrazino(1,2-a)-azepine.

2 g of the product obtained in 1. and 20 g of polyphosphoric acid (PPA) are heated for 1 hour at 100° C. After cooling down the mixture it is poured into ice-water and then extracted with ether. The ethereal layer is washed with water to neutral and subsequently dried and evaporated to dryness.

Yield: 1.8 g (100%); melting point 95°–100° C.
Melting point iodomethylate 285°–289° C.
Melting point HCl salt 264°–267° C (dec.).

3. By halogenating the hydroxyl group of the compound obtained in (1) with thionylchloride the corresponding chloro-compound is obtained. This chloro-compound is converted into the final product obtained in (2) in the manner as specified in (2) but in the presence of AlCl$_3$ instead of polyphosphporic acid. The total yield via both steps is about 60%.

The same compound is prepared by esterifying the hydroxyl group of the compound obtained in (1) with acetic acid and treating the acetoxy compound thus obtained in the manner as specified in (2) Total yield 65%.

The starting product required in (1) may be prepared in the following manner:

A.1. Preparation of β-hydroxy-N-methyl-N-hydroxyethylphenylethylamine (direct)

To 61 g of 2-methylaminoethanol in 70 ml of water are added dropwise 65 g of styrene oxide in such a manner that the temperature does not rise about 45° C. The mixture is then heated on a water bath for about 6 hours after which the excess of 2-methylaminoethanol is distilled off under reduced pressure (0.1 mm Hg). The oil obtained is dissolved in a small quanitity of benzene and then chromatographed on a silica-column (eluded with a mixture of ethyl alcohol:benzene (2:8), to which 2 drops of concentrated ammonia were added). After evaporating the solvent a light-brown coloured oil is obtained.

($N_D^{20}$ = 1,5365). Yield about 75%.

A.2. Preparation of β-hydroxy-N-methyl-N-hydroxyethylphenylethylamine (indirect)

a. To an aqueous solution of methylamine (72 ml; 40% solution) and 100 ml of ethanol are added dropwise 24 g of styrene oxide. The mixture is stirred for 3 hours at room temperature. Subsequently the solvents are evaporated and the residue distilled at a reduced pressure (0.2 mm Hg at 80°–85° C). Treatment of the oil obtained with pentane yields a crystalline substance.

Melting point β-hydroxy-N-methylphenylethylamine 65°–70° C. Yield 65%.

b. A solution of 75 g of the product obtained in a. and 26 g of ethylene oxide in 50 ml of absolute ethanol is heated for 18 hours at 60° C. After that the solvent is evaporated at reduced pressure and the oily residue chromatographed on a silica column (eluted with a mixture of benzene:ethyl-alcohol (1:1) to which 2 drops ammonia have been added.

After evaporation of the solvent a light-brown coloured oil is obtained (yield about 90%).

Rf in ethylalcohol:ammonia (9:1) = 0.67 on SiO$_2$. ($N_D^{20}$ = 1.5363).

B. Preparation of β-chloro-N-methyl-N-chloroethylphenylethylamine

To a solution of 20 g of the product obtained in (A) in 60 ml chloroform a solution of 40 ml thionylchloride in 60 ml of chloroform is added dropwise at 0° C.

While stirring the mixture is heated at 60° C for half an hour. Subsequently the solvent and the excess of thionylchloride are distilled off. The residue, added to ice water, is washed with ether three times and then made alkaline with the aid or sodium carbonate. The mixture is then extracted with ether and the ether extracts washed with water to neutral and dried. After evaporation of the ether a yellow coloured oil is obtained which without any additional purification is used for further conversion.

Yield about 75%. $N_D^{26}$ = 1.5291.

EXAMPLE II

In a similar manner the following compounds are prepared:
8-chloro-2(N)-methyl-1,2,3,4,10,14b-hexahydro-dibenzo(c,f)-pyrazino(1,2-a)-azepine.maleate; melting point 180°–185° C,
1,2,3,4,10,14b-hexahydro-dibenzo(c,f)-pyrazino(1,2-a)-azepine.HCl; melting point 289°–291° C,
8-methoxy-2(N)-methyl-1,2,3,4,10,14b-hexahydro-dibenzo(c,f)-pyrazino(1,2-a)-azepine.maleate; melting point 198°–199° C,
2(N)-propyl-1,2,3,4,10,14b-hexahydro-dibenzo(c,f)-pyrazino(1,2-a)-azepine.maleate; melting point 214°–216° C,
2(N),7-dimethyl-1,2,3,4,10,14b-hexahydro-dibenzo(c,f)-pyrazino(1,2-a)-azepine.maleate; melting point 230°–232° C,
8-hydroxy-2(N)-methyl-1,2,3,4,10,14b-hexahydro-dibenzo(c,f)-pyrazino(1,2-a)-azepine.maleate; melting point 247°–250° C,
2(N)-cyclopropylmethyl-1,2,3,4,10,14b-hexahydro-dibenzo (c,f)-pyrazino(1,2-a)-azepine.maleate; melting point 210°–213° C.
2(N)-dimethylaminoethyl-1,2,3,4,10,14b-hexahydro-dibenzo (c,f)-pyrazino(1,2-a)-azepine.dimaleate; melting point 137°–139° C (dec.),
2(N)-α-pyridinoethyl-1,2,3,4,10,14b-hexahydro-dibenzo(c,f)-pyrazino(1,2-a)-azepine.2 HCl; melting point 238°–242° C,
8-bromo-2(N)-methyl-1,2,3,4,10,14b-hexahydro-dibenzo(c,f)-pyrazino(1,2-a)-azepine.maleate; melting point 188°–191° C.
13-methyl-(2(N)-methyl-1,2,3,4,10,14b-hexahydro-dibenzo(c,f)-pryazino(1,2-a)-azepine.HCl; melting point 275° C (dec.),
13-chloro-2(N)-methyl-1,2,3,4,10,14b-hexahydro-dibenzo(c,f)-pyrazino(1,2-a)-azepine; melting point 123°–125° C,
11-methoxy-2(N)-methyl-1,2,3,4,10,14b-hexahydro-dibenzo(c,f)-pyrazino(1,2-a)-azepine.maleate; melting point 189°–194° C,
13-methoxy-2(N)-methyl-1,2,3,4,10,14b-hexahydro-dibenzo(c,f)-pyrazino(1,2-a)-azepine.HCl; melting point 270°–272° C,
2(N)-ethyl-1,2,3,4,10,14b-hexahydro-dibenzo(c,f)-pyrazino(1,2-a)-azepine.HCl; melting point 280°–286° C,
12-chloro-2(N)-methyl-1,2,3,4,10,14b-hexahydro-dibenzo(c,f)-pyrazino(1,2-a)-azepine.HCl; melting point >290° C.

EXAMPLE III

1. β-[(O-hydroxymethyl)-anilino]-N-methylphenylethylamine

To a solution of 12.3 g of O-amino-benzylalcohol in 100 ml ethanol:water (95:5) and 16 g pyridine (0.2 mol) is added dropwise a solution of 20.6 g of β-chloro-N-methylphenylethylamine.HCl in 100 ml ethanol:water (95:5). The mixture is then refluxed for 12 hours. The mixture is then cooled down, after which the solvent is evaporated. The residue is poured in water and washed with ether three times. The water layer is made alkaline with 2N sodium hydroxide and subsequently extracted with ether three times. The ether extracts are washed with water, dried and evaporated. The residue is used without any additional purification.

Rf in alcohol:toluene (1:9) = 0.55 on $SiO_2$.

2. 1(N)-[(O-hydroxymethyl)-phenyl]-2-phenyl-4(N')-methylpiperazine

To 400 ml of 1,2-dibromoethane at 100° C is added drop-wise a solution of 10 g of the product obtained in (1) in 30 ml of pyridine after which the mixture is left stand at this temperature for 20 minutes.

Then pyridine and the excess of dibromoethane are distilled off in vacuo after which the residue is poured into water and washed with ether. Subsequently the water layer is made alkaline with sodiumcarbonate and extracted with ether.

The ether layer is washed with water, dried and evaporated. Melting point 90°–94° C. Yield 60%.

The same product is obtained by reacting the compound obtained in (1) with ethylchloroacetate or diethyl oxalate and reducing the mono- or di-oxo-compound thus obtained with $LiAlH_4$.

3. 2(N)-methyl-1,2,3,4,10,14b-hexahydro-dibenzo(c,f)-pyrazino(1,2-a)-azepine In the manner as in example (I.2.) the product obtained in (2) is converted into the final product mentioned above.

Melting point 96°–100° C. Yield 95%. Melting point of the HCl salt 265° C.

EXAMPLE IV

In a similar manner as indicated in example III the following compounds are prepared:
8-methoxy-2(N)-methyl-1,2,3,4,10,14b-hexahydro-dibenzo(c,f)-pyrazino(1,2-a)-azepine.maleate; melting point 196°–199° C.
2(N)-propyl-1,2,3,4,10,14b-hexahydro-dibenzo(c,f)-pyrazino(1,2-a)-azepine.maleate; melting point 212°–215° C.

EXAMPLE V

γ-chloro-N-methyl-phenylpropylamine

To a cooled suspension of 20 g of γ-hydroxy-N-methylphenylpropylamine.HCl in chloroform are added dropwise 30 ml of thionylchloride. The mixture is subsequently stirred at room temperature till all solid substance has been dissolved. The solvent chloroform and the excess of thionylchloride are distilled off after which the residue is washed with ether and then made alkaline (pH = 8) with a sodiumcarbonate solution (10%). The alkaline solution is subsequently extracted with ether and the ether extracts washed with water, dried and evaporated to dryness. The residue (oil) is used without any additional purification (yield 15.6 g; 85%).

2. γ[(O-hydroxymethyl)-anilino]-N-methyl-phenylpropylamine

In the same way as described in example (III.1) 13.8 g of the oil obtained in (1) are reacted with O-amino-benzyl-alcohol dissolved in ethanol:water (95:5) to which 6 g of pyridine have been added. The product obtained (a yellow coloured oil) is further converted without any purification.

Rf in ethylalcohol:toluene (1:9) = 0.5. Yield 70% (14.1 g).

3. 3(N)-[(O-hydroxymethyl)-phenyl]-4-phenyl-1(N)-methylhexahydropyrimidine

A solution of 13.5 g of the oil obtained in (2) in an aqueous formaldehyde solution is stirred for 1.5 hours at about 75° C.

Subsequently the mixture is diluted with water and extracted with ether three times. The ether extracts are washed, dried and evaporated to dryness. The oily residue (13.4 g, 95%) is used without further purification.

The same product is obtained if methylenechloride, dissolved in dimethylsulfoxide to which some drops of triethylamine have been added, is used instead of the aforesaid aqueous formaldehyde-solution. The same product is also obtained by using ethylchloroformate instead of methylene chloride and reducing the oxo-compound thus obtained with $LiAlH_4$.

4. 3(N)-methyl-1,2,3,4,10,14b-hexahydro-dibenzo(c,f)-pyrimidino(3,4-a)-azepine In a similar manner as indicated in example (I.2) the product obtained in 3. is converted into the above-mentioned final product.

Yield (oil) 75%. Melting point fumarate 188°–191° C (dec.).

EXAMPLE VI

In a similar manner as described in example V the following compounds are prepared:
1,2,3,4,10,14b-hexahydro-dibenzo(c,f)-pyrimidino(3,4-a)-azepine.HCl; melting point 212°–217° C,
3(N)-methyl-7-trifluoromethyl-1,2,3,4,10,14b-hexahydrodibenzo(c,f)-pyrimidino(3,4-a)-azepine,
(−) 3(N)-methyl-1,2,3,4,10,14b-hexahydro-dibenzo(c,f)-pyrimidino(3,4-a)-azepine.fumarate; melting point 185°–188° C, $[\alpha]_D^{20} = -333°$,
(+) 3(N)-methyl-1,2,3,4,10,14b-hexahydro-dibenzo(c,f)-pyrimidino(3,4-a)-azepine.fumarate; melting point 184°–187° C, $[\alpha_D^{20}] = +335°$,
3(N)-ethyl-1,2,3,4,10,14b-hexahydro-dibenzo(c,f)-pyrimidino (3,4-a)-azepine.HCl; melting point 198°–201° C.

EXAMPLE VII

2(N)-methyl-1,2,3,4,10,14b-hexahydro-dibenzo(c,f)-pyrazino (1,2-a)-azepine 1 g of 1(N)[(O-hydroxymethyl)-phenyl]-2-phenyl-4(N')-methyl-piperazine is added in small portions, while stirring, to 3 ml of concentrated sulphuric acid at room temperature.

The reaction is strongly exothermic so that the mixture has to be cooled a little to keep the mixture at ambient temperature.

The mixture is then stirred for another 2 hours and subsequently poured in ice-water. The aqueous mixture is made alkaline with concentrated ammonia, after which it is extracted with ether. The ether layers are washed, dried and evaporated to dryness.

Melting point 90°–95°C. Yield 90%.

Flow Sheet

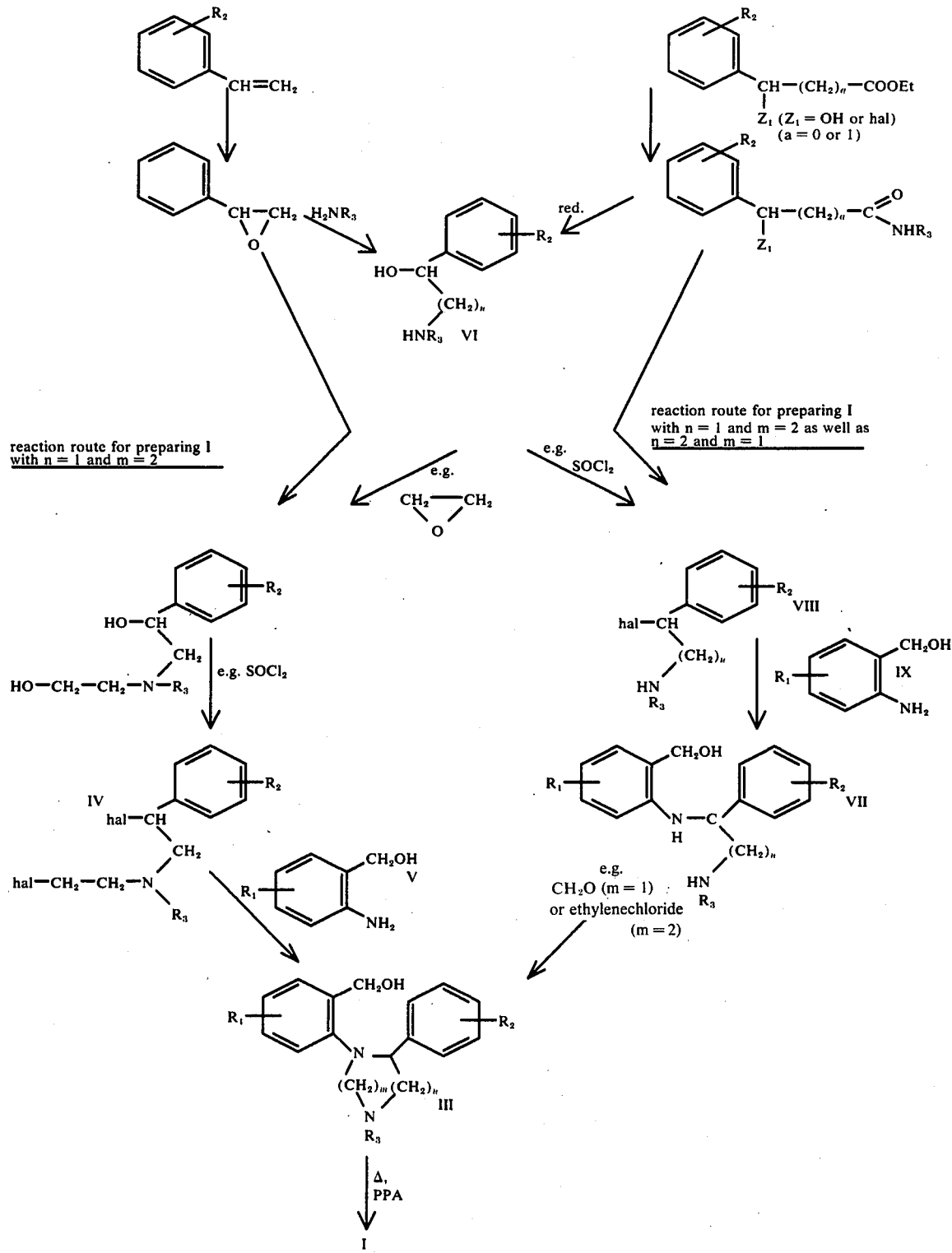

I claim:
1. Process for the preparation of a compound of the formula:

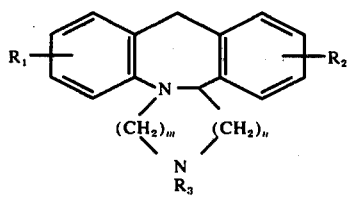

I in which
 n is the number 1 or 2,
 m is the number 1 if n = 2, and the number 2 if n = 1,
 $R_1$ and $R_2$ are selected from the group consisting of hydrogen, hydroxy, halogen, alkyl having 1 to 4 carbon atoms, alkoxy having 1 to 4 carbon atoms, and trifluoromethyl,
 $R_3$ is selected from the group consisting of hydrogen and alkyl having 1 to 6 carbon atoms,
which comprises ring-closing a compound of the formula:

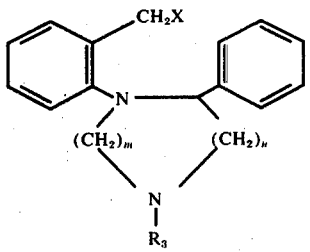

III or a salt thereof, in which $n$, $m$, $R_1$, $R_2$ and $R_3$ have the aforesaid meanings, and X is selected from the group consisting of hydroxy, chlorine, bromine, iodine and esterified hydroxy, in the presence of an acid or a Lewis acid and recovering the desired compound from the reaction mixture.

2. The process according to claim 1 in which a compound of formula III is used in which X represents a hydroxy group.

3. Process according to claim 1 in which the ring closure is carried out in the presence of a member of the group consisting of polyphosphoric acid, phosphorus trioxide, and phosphorus pentoxide.

4. The process according to claim 1 in which the esterified hydroxy group is acetoxy.

* * * * *